US00PP31186P2

(12) United States Plant Patent
Stemkens

(10) Patent No.: US PP31,186 P2
(45) Date of Patent: Dec. 3, 2019

(54) ***LAVANDULA* PLANT NAMED 'LAAZ0008'**

(50) Latin Name: *Lavandula angustifolia*
Varietal Denomination: LAAZ0008

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/999,978

(22) Filed: Sep. 6, 2018

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./445
See application file for complete search history.

(56) References Cited

PUBLICATIONS

UPOV hit on *Lavandula* plant named, 'LAAZ0008', QZ PBR 20182019, filed Aug. 3, 2018.*

* cited by examiner

*Primary Examiner* — Anne Marie Grunberg
(74) *Attorney, Agent, or Firm* — Dale Skalla

(57) ABSTRACT

A new *Lavandula* plant named 'LAAZ0008' particularly distinguished by deep-purple flowers, a very long flowering season, dark green foliage, medium flower stems, medium sized plants with a well-branched and upright habit. The plant is very early to flower because it does not need cold to flower

1 Drawing Sheet

Figure 1:
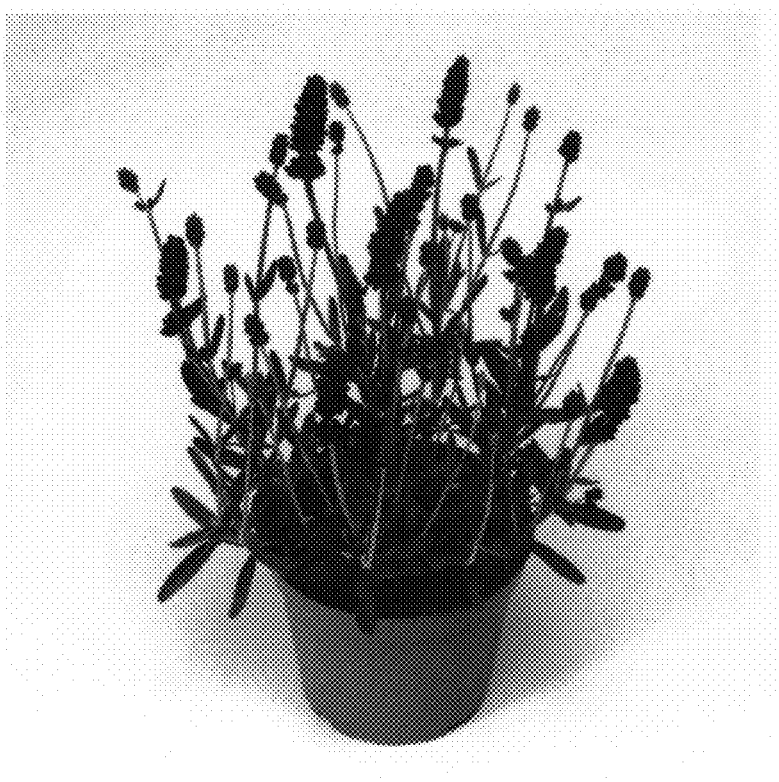

Latin name of the genus and species of the plant claimed: *Lavandula angustifolia.*
Varietal denomination: 'LAAZ0008'.

BACKGROUND OF THE NEW PLANT

The present invention comprises a new *Lavandula*, botanically known as *Lavandula angustifolia*, and hereinafter referred to by the variety name 'LAAZ0008'.

'LAAZ0008' is a product of a planned breeding program. The new cultivar has deep-purple flowers, a very early flowering, a long flowering season, dark green broad foliage with a bit greyish hue, medium flower stems, large sized plants with a well-branched and upright habit. The plant is very resistant to cold.

'LAAZ0008' originated from a pollination made in July 2012 in a greenhouse in Enkhuizen, The Netherlands.

The female parent was the unpatented, proprietary plant designated 'R2731-2', with light blue flowers, a less branching habit, grey foliage and flowering 18 days later when compared to 'LAAZ0008'.

The male parent of 'LAAZ0008' is an unknown cloud of pollen from the whole population The resultant seed was sown in January 2013 and grown outdoors in Enkhuizen, The Netherlands. 'LAAZ0008' was selected as a single flowering plant within the progeny of the stated cross on July 5 in Enkhuizen, The Netherlands.

The first act of asexual reproduction of 'LAAZ0008' was accomplished when vegetative cuttings were propagated from the initial selection July 2013 in a greenhouse in Enkhuizen, The Netherlands.

BRIEF SUMMARY OF INVENTION

Horticultural examination of plants grown from cuttings of the plant initiated in July 2013, and continuing thereafter, has demonstrated that the combination of characteristics as herein disclosed for 'LAAZ0008' are firmly fixed and are retained through successive generations of asexual reproduction.

'LAAZ0008' has not been observed under all possible environmental conditions. The phenotype may vary significantly with variations in environment such as temperature, light intensity and day length.

A Plant Breeder's Right for this cultivar has not yet been applied for. 'LAAZ0008' has not been made publicly available prior to the effective filing date of this application, notwithstanding any disclosure that may have been made less than one year prior to the effective filing date of this application by the inventor or another who obtained 'LAAZ0008' directly from the inventor.

The following traits have been repeatedly observed and are determined to be basic characteristics of the new variety. The combination of these characteristics distinguishes this *Lavandula* as a new and distinct variety.

BRIEF DESCRIPTION OF THE PHOTOGRAPHS

The accompanying photographic drawings show typical flower and foliage characteristics of 'LAAZ0008' with colors being as true as possible with an illustration of this type. The photographic drawings show in FIG. 1 a whole flowering plant from an outdoor trial and in FIG. 2 a close view of an inflorescence.

DETAILED BOTANICAL DESCRIPTION

The plant descriptions and measurements were taken outdoors in Enkhuizen, The Netherlands on Jun. 28, 2018 on about 14 week old plants. Rooted cuttings had been planted, one plant per pot, in 13 cm pots in week 35, 2016. The plants were pinched.

Figure 2:
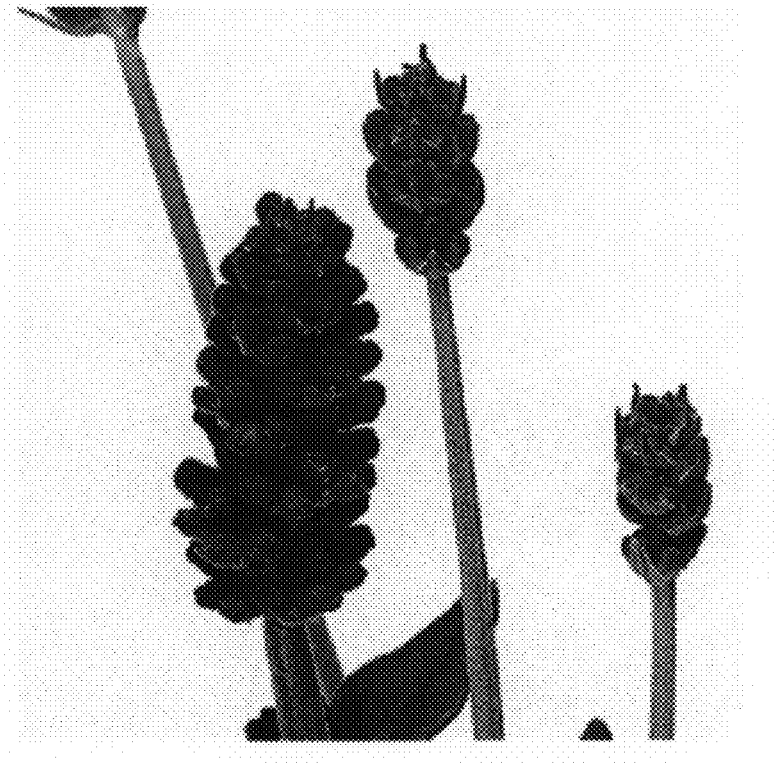

The aforementioned photographs: FIGS. 1 and 2 were taken in Enkhuizen, The Netherlands, and using an about 12 week old plant in a 13 cm pot from an outdoor trial.

Color references are made to The Royal Horticultural Society Colour Chart (R.H.S.) 2001.

TABLE 1

DIFFERENCES BETWEEN THE NEW VARIETY 'LAAZ0008' AND A MOST SIMILAR VARIETY

| | 'LAAZ0008' | 'LABLUSA' (U.S. Plant Pat. No. 19,765) |
|---|---|---|
| Flower color: | Deep-purple | Blue |
| Leaf width: | Broad | Narrow |
| Length of peduncle: | Up to 7 cm | Up to 18 cm |

Plant:

*Form, growth and habit.*—Vigorous, upright, freely branching.

*Plant height.*—18.0-24.0 cm.

*Plant height (inflorescence included).*—About 33.0 cm.

*Plant width.*—About 35.0 cm.

Roots:

*Number of days to initiate roots.*—About 10 days at about 20 degrees C.

*Number of days to produce a rooted cutting.*—3-4 weeks at 18 degrees C.

*Type.*—Fine, fibrous, free branching.

*Color.*—RHS 155D.

Foliage:

*Type.*—Opposite; decussate, sessile.

*Fragrance.*—Strong.

*Immature, leaf color, upper surface.*—RHS 137B.

*Immature, leaf color, lower surface.*—RHS 137C.

*Mature, leaf color, upper surface.*—RHS 138B.

*Mature, leaf color, lower surface.*—RHS 139C.

*Length.*—3.1-3.3 cm.

*Width.*—1.1 cm.

*Shape.*—Ligulate.

*Base shape.*—Sessile.

*Apex shape.*—Acute.

*Margin.*—Entire.

*Texture, upper surface.*—Pubescent.

*Texture, lower surface.*—Pubescent.

*Color of veins, upper surface.*—RHS 142C.

*Color of veins, lower surface.*—RHS 143C.

Stem:

*Number of main stems per plant.*—About 12-18.

*Color of stem.*—RHS N138B.

*Length of stem.*—About 14.0-19.0 cm.

*Diameter.*—0.4 cm.

*Length of internodes.*—2.8-4.2 cm.

*Shape of stem.*—Square.

*Strength.*—Good.

*Texture.*—Pubescent.

*Peduncle color.*—RHS N138B.

*Peduncle length.*—About 15.0 cm.

*Peduncle diameter.*—0.2 cm.

*Peduncle strength.*—Strong.

*Peduncle texture.*—Pubescent.

Inflorescence:

*Flowering season.*—From June until October.

*Type.*—Flowers in long spikes, terminal on stems; flowers stay open all day.

*Number of open flowers per inflorescence.*—About 110 in various stages of development.

*Quantity of inflorescences per plant.*—About 20-29.

*Lastingness of individual blooms on the plant.*—About 3 days.

Bud (when first showing color):

*Color.*—RHS 89A.

*Length.*—0.4 cm.

*Width.*—0.3 cm.

*Shape.*—Oval.

Corolla:

*Immature, color of petals, upper surface.*—RHS 90B.

*Immature, color of petals, lower surface.*—RHS 90B.

*Spike horizontal diameter.*—2.2 cm.

*Spike height.*—6.6 cm.

*Mature, color of petals, upper surface.*—RHS 92A.

*Mature, color of petals, lower surface.*—RHS 92A.

*Petal length.*—0.3 cm.

*Petal diameter.*—0.2 cm.

*Apex.*—Obtuse.

*Margin.*—Entire.

*Shape.*—Rounded.

*Base.*—Fused.

*Degree of lobation.*—Moderate.

*Texture, upper surface.*—Glabrous.

*Texture, lower surface.*—Glabrous.

*Corolla tube, color, outer surface.*—RHS 84B and RHS N155C.

*Corolla tube, color, inner surface.*—RHS 84B and RHS N155B.

*Corolla tube length.*—0.3 cm.

*Diameter (at opening).*—0.2 cm.

*Corolla tube texture, outer surface.*—Glabrous.

*Corolla tube texture, inner surface.*—Glabrous.

Calyx:

*Form.*—All sepals fused to form tube around the corolla.

*Color.*—RHS N90A.

*Length of tube.*—0.3 cm.

*Width of tube.*—0.2 cm.

*Texture, outer surface.*—Pubescent.

*Texture, inner surface.*—Glabrous.

Reproductive organs:

*Number of stamens.*—4.

*Filament color.*—RHS 155C.

*Filament length.*—0.2 cm.

*Filament diameter.*—0.05 cm.

*Anther color.*—RHS N166A.

*Anther length.*—0.05 cm.

*Anther shape.*—Reniform.

*Pollen color.*—RHS 163C.

*Pollen amount.*—Sparse.

*Pistil.*—1 per flower.

*Pistil length.*—0.3 cm.

*Style color.*—RHS 150C.

*Style length.*—0.2 cm.

*Stigma color.*—RHS N199C.

Fertility/seed set: Has not been observed.

Disease/pest resistance: Has not been observed.

What is claimed is:

1. A new and distinct cultivar of *Lavandula* plant named 'LAAZ0008', as substantially illustrated and described herein.

* * * * *